(12) United States Patent
Feagin

(10) Patent No.: US 6,354,104 B1
(45) Date of Patent: Mar. 12, 2002

(54) LOCKABLE SPECIMEN TRANSPORTER

(76) Inventor: Darrell L. Feagin, P.O. Box 4326, Tallahassee, FL (US) 32315

( * ) Notice: Subject to any disclaimer, the term of this patent is extended or adjusted under 35 U.S.C. 154(b) by 0 days.

(21) Appl. No.: 09/769,574

(22) Filed: Jan. 26, 2001

(51) Int. Cl.[7] ............................................... F25D 3/08
(52) U.S. Cl. ........................ 62/457.1; 70/68; 220/210
(58) Field of Search ............................ 62/457.1, 457.7, 62/457.9; 220/210, 315, 254, 524; 70/63, 68, 167, 168, 169

(56) References Cited

U.S. PATENT DOCUMENTS

| | | | | |
|---|---|---|---|---|
| 2,942,450 A | * | 6/1960 | Krug | ............................ 70/68 |
| 4,955,957 A | * | 9/1990 | Homes | ........................ 220/324 |
| 5,319,937 A | * | 6/1994 | Fritsch et al. | ................. 61/3.62 |
| 5,845,515 A | * | 12/1998 | Nelson | ........................ 62/457.7 |
| 6,077,587 A | * | 6/2000 | Potok | ............................ 70/62 |
| 6,237,765 B1 | * | 5/2001 | Hagen et al. | .......... 206/315.11 |
| 6,247,328 B1 | * | 6/2001 | Mogil | ........................ 62/457.2 |

\* cited by examiner

Primary Examiner—William E. Tapolcai
(74) Attorney, Agent, or Firm—John Wiley Horton

(57) ABSTRACT

A lockable blood and urine sample transporter. The transporter has a thermostatically controlled cooling unit which maintains the specimens at a fixed temperature. The transporter also has a securing lock which prevents unauthorized access to the specimens contained therein.

5 Claims, 13 Drawing Sheets

LOCKABLE SPECIMEN TRANSPORTER

BACKGROUND—FIELD OF INVENTION

This invention relates to the field of blood and urine testing. More specifically, the invention comprises a lockable and portable specimen transporter. The transporter has a thermostatically controlled cooling unit which maintains the specimens at a fixed temperature. The transporter also has a securing lock which prevents unauthorized access to the specimens contained therein.

BACKGROUND—DESCRIPTION OF PRIOR ART

Blood and urine testing is an expanding field. Employers are now conducting drug screens of their employees. General blood testing is also performed for the purpose of obtaining health and life insurance. Collection of the samples is often performed on site. The samples must then be transported to a laboratory where the testing is conducted. If there is a significant delay between collection and testing, refrigeration of the samples is required.

The practical aspects of specimen collection and transportation are further complicated by the fact that many statutes apply to the preservation of samples which are to be used in evidence. These statutory requirements, often called "chain of custody" requirements, mandate that the samples must be maintained in a secure vessel from the time of collection to the time of testing.

Numerous prior art devices exist for the transportation of biological specimens. U.S. Pat. No. 5,040,678 to Lenmark (1991) discloses a hollow transport container having a number of pre-cut foam inserts. The focus of this device is cushioning the specimens from impact. It does not refrigerate the specimens, nor does it provide secure storage.

Refrigeration is provided in U.S. Pat. No. 5,217,064 to Kellow et.al. (1993). The '064 device is intended to safely store temperature-sensitive pharmaceuticals in an ambulance or the like. It provides thermostatically controlled refrigeration, as well as an alarm that sounds if the storage temperature is exceeded for a set length of time (indicating that the pharmaceuticals need to be discarded). The invention also provides that the temperature alarm can only be reset with a key. However, the '064 device does not provide any mechanism to prevent unauthorized access.

A small and relatively simple specimen transporter is disclosed in U.S. Pat. No. 5,405,012 to Shindler et.al. (1995). The base of the '012 device is configured to be molded from styrene or Styrofoam. Refrigeration is provided by the addition of a "cold pack" (commonly an enclosed container in which an irreversible chemical reaction produces cold temperatures). While it is capable of maintaining cool temperatures for some time, the lack of a controlled refrigeration system limits the time the specimens can be safely stored within the device. It also lacks any anti-tamper mechanism.

A very simple and potentially disposable specimen storage device is disclosed in U.S. Pat. No. 5,435,142 to Silber (1995). This device is well-suited to packaging and shipping of specimens via common carriers. It is not sufficiently durable for long term use, nor is it capable of preventing unauthorized access.

A more sophisticated specimen transporter is disclosed in U.S. Pat. No. 5,483,799 to Dalto (1996). This device features a thermostatically controlled heat sink mechanism capable of heating or cooling the storage compartment. It employs logic circuitry to allow user-defined minimum and maximum temperatures. It does not include any type of securing mechanism which would prevent unauthorized access.

A different approach to specimen transport is disclosed in U.S. Pat. No. 5,918,478 (1999) and U.S. Pat. No. 6,062,040 (2000) to Bostic et.al. These patents disclose a double-walled closed container. The space between the walls can be evacuated to provide insulation, and to prevent tampering. The device includes a pneumatic hand pump used to evacuate the container upon sealing. It also includes structural foam placed between the walls to prevent collapse when the vacuum is introduced. Neither device is capable of maintaining reduced temperatures indefinitely. Although the pneumatic sealing approach does provide some security, it is impractical for a container which must be opened periodically to admit new specimens (as it would have to be re-evacuated after each opening).

The known methods for securely transporting biological specimens are therefore limited in that they:

1. Cannot maintain reduced temperatures indefinitely;
2. Do not provide sufficient anti-tamper means;
3. Cannot be opened regularly to admit new specimens;
4. Do not provide separate storage areas for different types of specimens; and
5. Do not allow for a variety of power sources.

OBJECTS AND ADVANTAGES

Accordingly, several objects and advantages of the present invention are:

1. To maintain reduced temperatures indefinitely;
2. To provide sufficient anti-tamper means;
3. To allow the storage vessel to be opened regularly to admit new specimens;
4. To provide separate storage areas for different types of specimens; and
5. To allow for a variety of power sources.

DRAWING FIGURES

Figure 1:
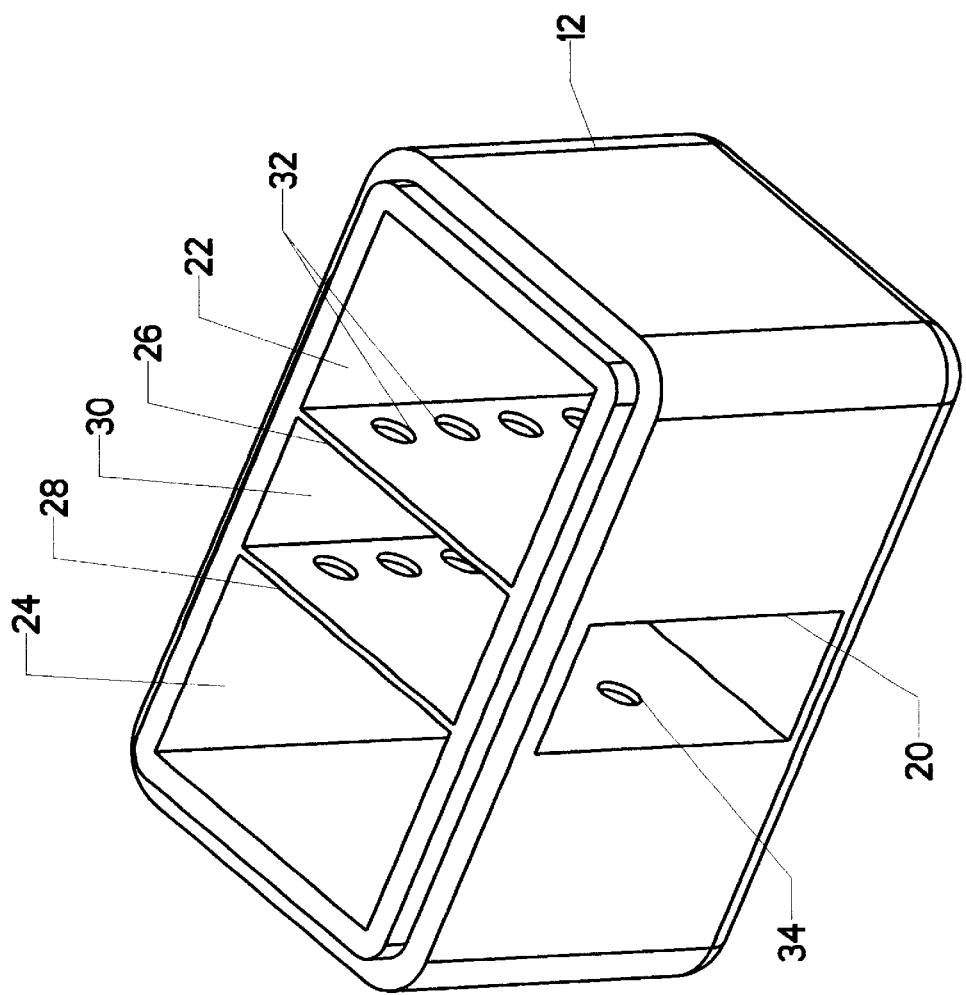
FIG. 1 is an isometric view, showing the chassis of the proposed transporter.

| Reference Numerals in Drawings | | | |
|---|---|---|---|
| 10 | transporter | 12 | chassis |
| 14 | cooling module | 16 | battery |
| 18 | top | 20 | center slot |
| 22 | blood sample well | 24 | urine sample well |
| 26 | right bulkhead | 28 | left bulkhead |
| 30 | center cavity | 32 | cooling port |
| 34 | return port | 36 | cooling intake |
| 38 | circulation fan | 40 | right hatch |
| 42 | left hatch | 44 | right hatch cover |
| 46 | left hatch cover | 48 | urine sample tray |
| 50 | finger notch | 52 | blood sample tray |
| 54 | blood vial | 56 | vial cavity |
| 58 | target vector | 60 | power switch |
| 62 | power input | 64 | indicator lights |
| 66 | cooling outlet | 68 | fabric cover |
| 70 | access hole | 72 | securing flap |
| 74 | zipper track | 76 | zipper handle |
| 78 | zipper lock | 80 | strap attachment |
| 82 | document slot | | |

DESCRIPTION

FIG. 1 shows chassis 12, which is essentially an elongated box having an insulated bottom and for insulated side walls. The interior of chassis 12 is subdivided by right bulkhead 26 and left bulkhead 28. The resulting subdivisions are urine sample well 24, center cavity 30, and blood sample well 22. Right bulkhead 26 and left bulkhead 28 each have a series of cooling ports 32 passing completely through them. These ports allow air within center cavity 30 to flow into urine sample well 24 and blood sample well 22. Each bulkhead is also cut by a return port 34 (only one of the two return ports 34 may be observed in FIG. 1), the function of which will be explained subsequently. The front wall of chassis 12 is cut by center slot 20, which allows external access to center cavity 30.

Figure 1B:
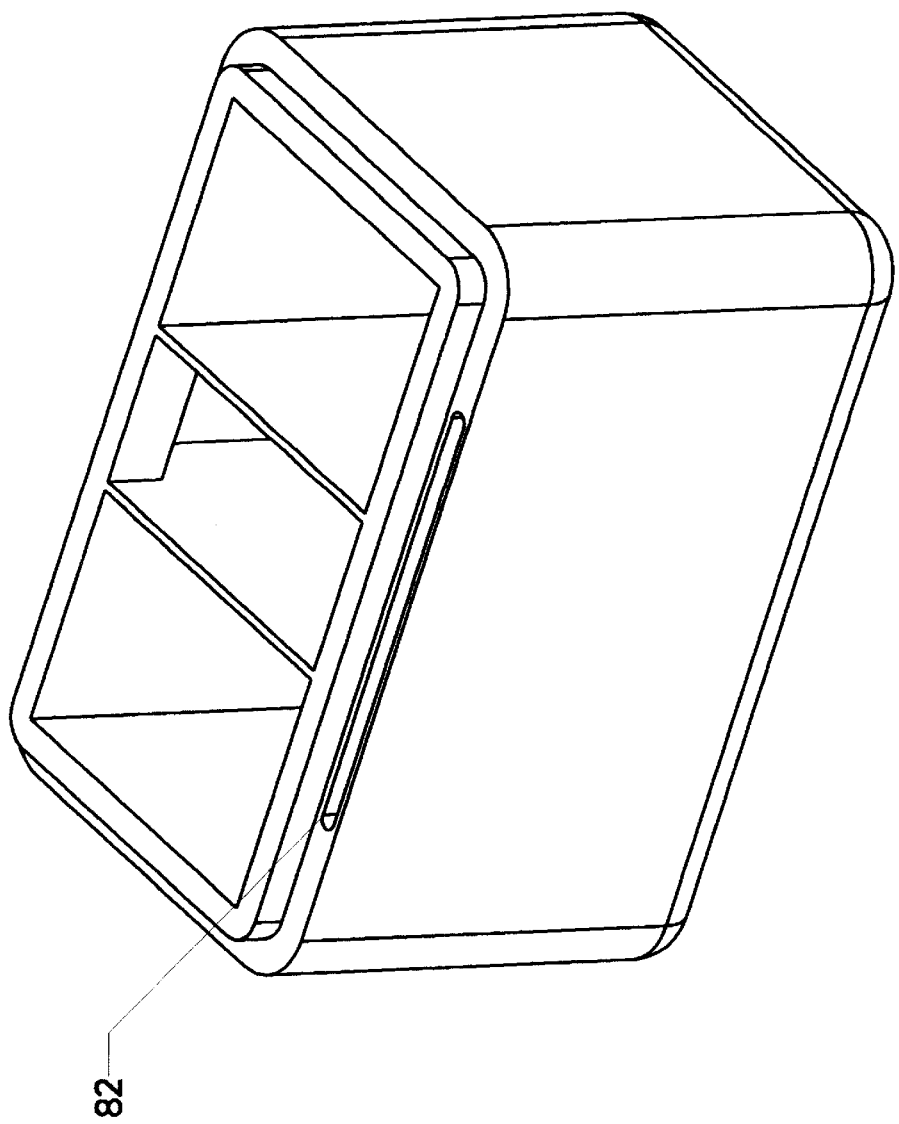
FIG. 1B is an isometric view, showing the chassis from another angle.

FIG. 1B shows chassis 12 from another angle. Document slot 82 is provided to house the documentation accompanying the specimens.

Figure 2:
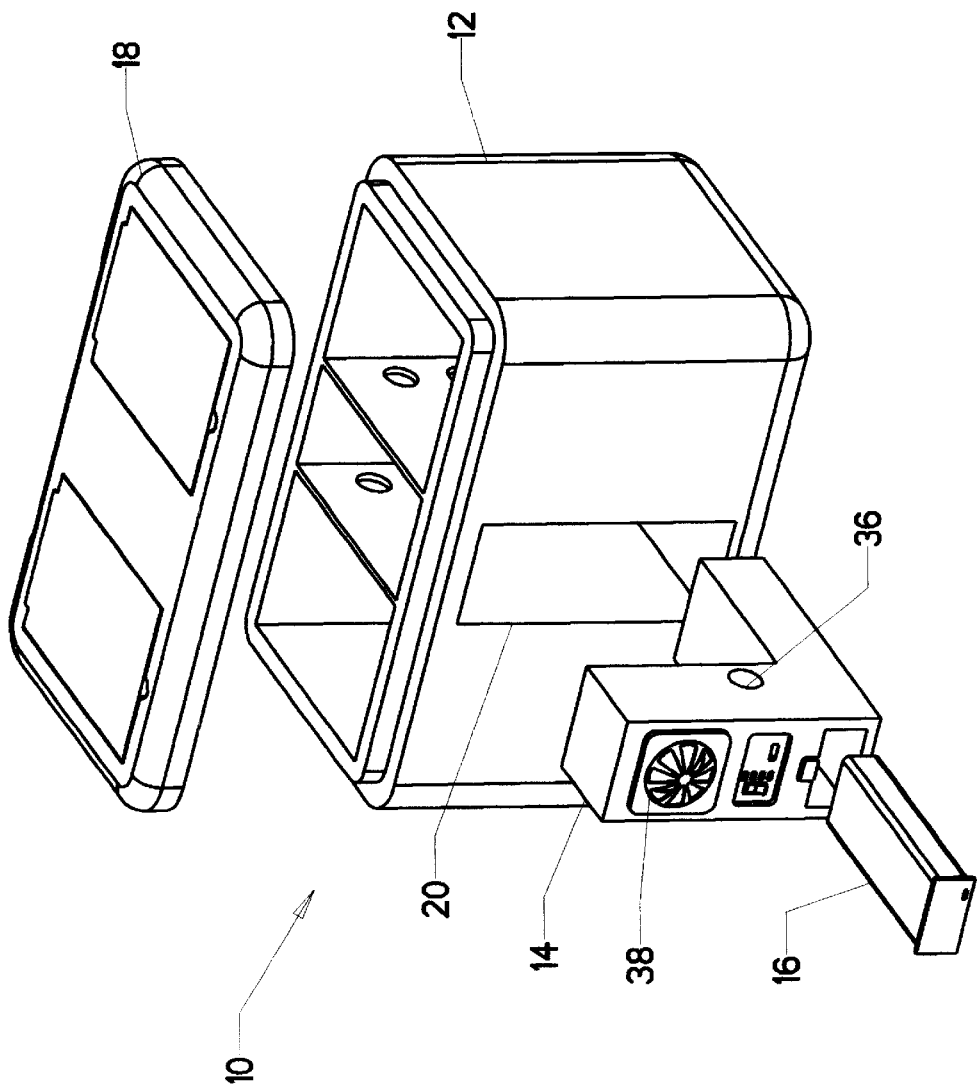
FIG. 2 is an isometric view, showing the major components of the present invention.

FIG. 2 depicts the major elements of specimen cooler 10. Cooling module 14 is configured to slide through center slot 20, coming to rest within center cavity 30. Cooling module 14 is fixed in place by convention a means—since it does not normally need to be removed throughout the life of the device. Cooling module 14 contains an electrically-driven cooling unit, which may, without limitation, be of the vapor-loop or thermocouple type. For purposes of general discussion, the cooling unit will be taken to contain an internal heat exchanger, which absorbs heat from the interior of chassis 12, whereafter it is conveyed to an external heat exchanger, which expels the heat to the surrounding air. Those skilled in the art will realize that these heat exchangers may be of several different types.

Circulation fan 38 provides two functions. It actually employs two sets of fan blades, one circulating air on the outside of chassis 12 and one circulating air on the inside of chassis 12. Both sets of blades are mounted on a common shaft and driven by a common motor (for cost saving purposes). The external set of fan blades circulates external air over the external heat exchanger, thereby expelling heat to the surrounding air. The internal set of fan blades circulates internal air over the internal heat exchanger, thereby cooling that air and cooling the contents of chassis 12.

Figure 4:
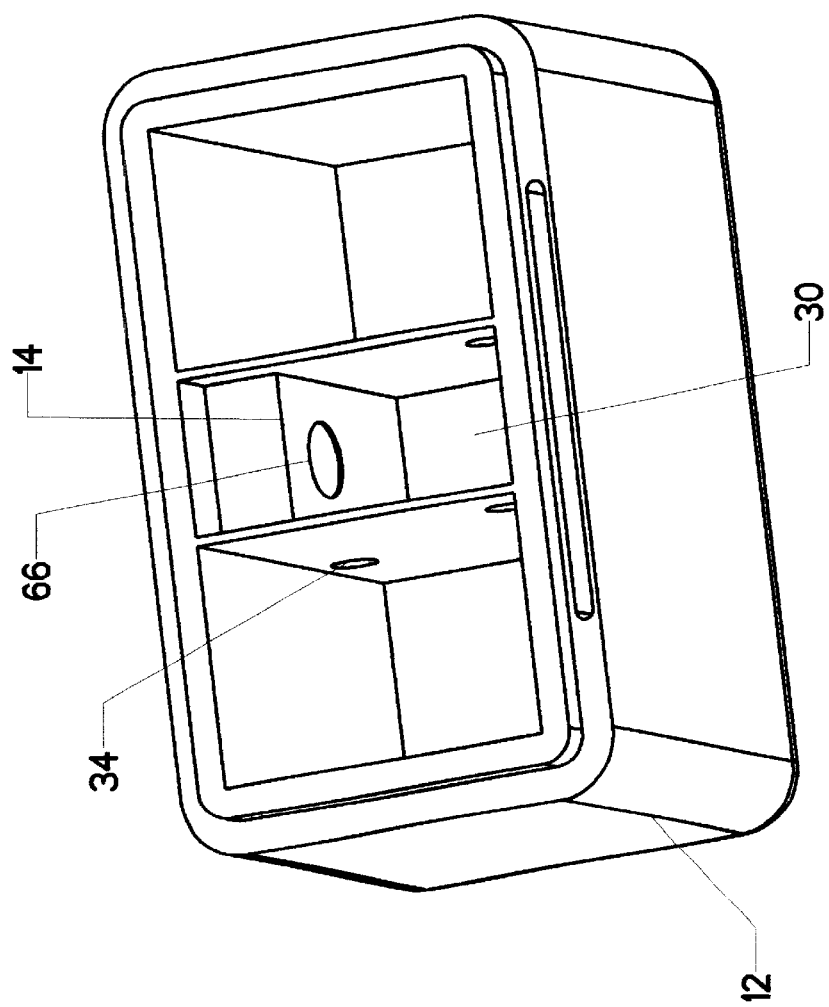
FIG. 4 is an isometric view, showing the cooling circulation of the present invention.

Cooling module 14 has a pair of cooling intakes 36—one on either side. Cooling intakes 36 align with return ports 34 in the two bulkheads. Turning briefly now to FIG. 4, the circulation of air within chassis 12 will be explained. Cooling module 14 has cooling outlet 66. The internal set of fan blades blows cold air out of cooling outlet 66, as shown by the arrow. This results in a positive pressure within central cavity 30, which causes the cool air to flow through cooling ports 32 and into urine sample well 24 and blood sample well 22. The air within the two wells is then pulled back into cooling module 14 by return ports 34. In this manner, air is circulated within the interior of chassis 12 so that cooling module 14 can regulate the temperature within chassis 12.

Returning now to FIG.2, the reader will observe that cooling module has detachable battery 16. This is provided so that refrigeration will not be interrupted during periods when transporter 10 cannot be plugged into external power. Battery 16 is designed to be easily removed and replaced. The user can carry multiple batteries to extend the time during which transporter 10 can operate exclusively on internal power.

Top 18 covers the upward-facing opening of chassis 12. It is configured to be secured in place. The user does not normally remove top 18, though it can be configured for easy removal in order to aid cleaning and the like.

Figure 2B:
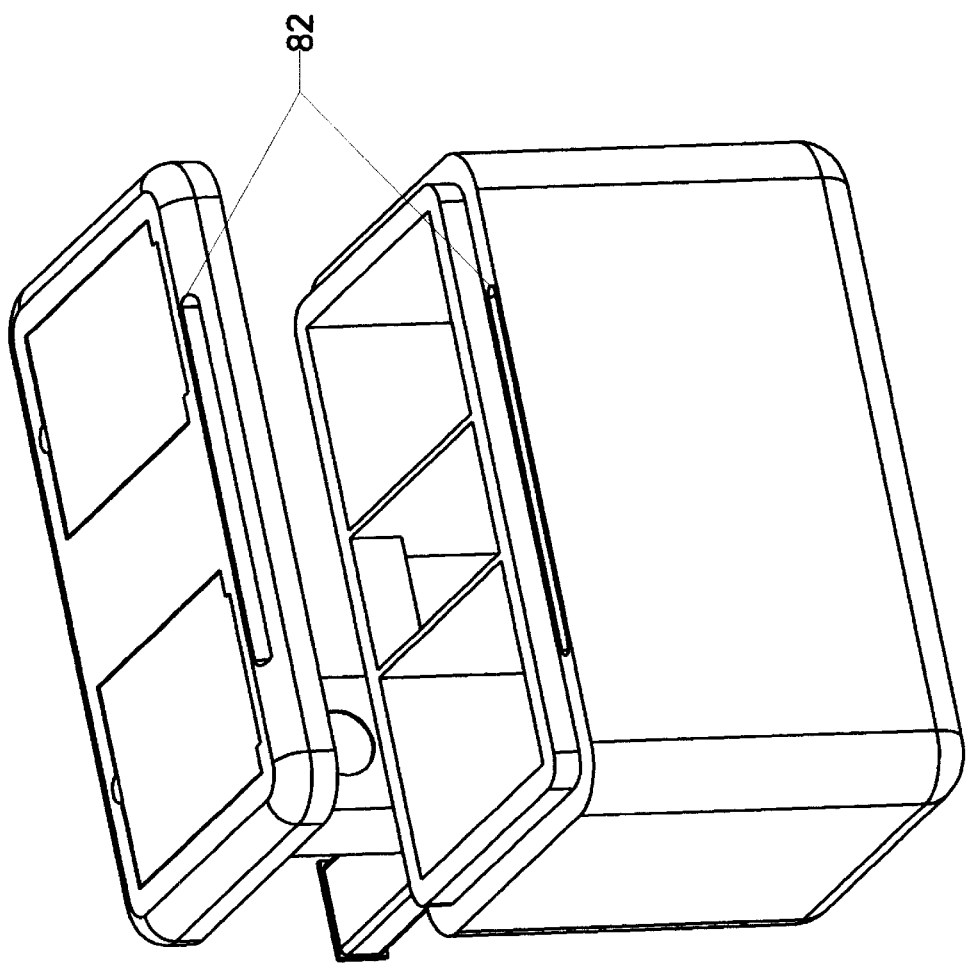
FIG. 2B is an isometric view, showing the invention from another angle.

FIG. 2B shows the same components from another perspective. The reader will observe that document slot 82 passes through top 18. This allows the user to place documentation in document slot 82 while top 18 is in place on chassis 12.

Figure 3:
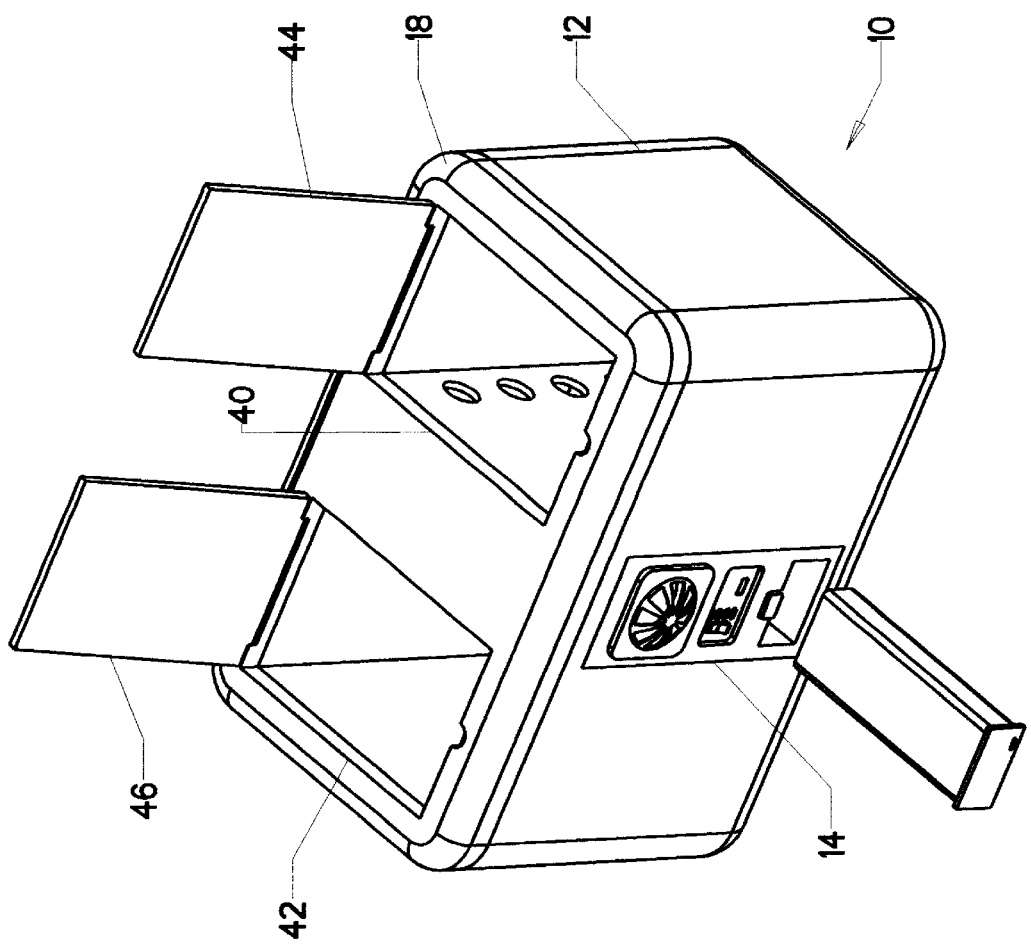
FIG. 3 is an isometric view, showing the assembled components of the present invention.

FIG. 3 shows transporter 10 with all its structural components assembled. Cooling module 14 is affixed in place, as is top 18. Top 18 has two openings—right hatch 40 and left hatch 42. Each hatch has a hinged cover—right hatch cover 44 and left hatch cover 46. Both hatch covers are shown in the open position in FIG. 3. Both hatch covers may be closed over both hatches, being fastened in place by plastic snaps or other conventional means. Once the user presses a hatch cover into the closed position, the fastening means will retain it in the closed position until the user desires to open it again.

Figure 5:
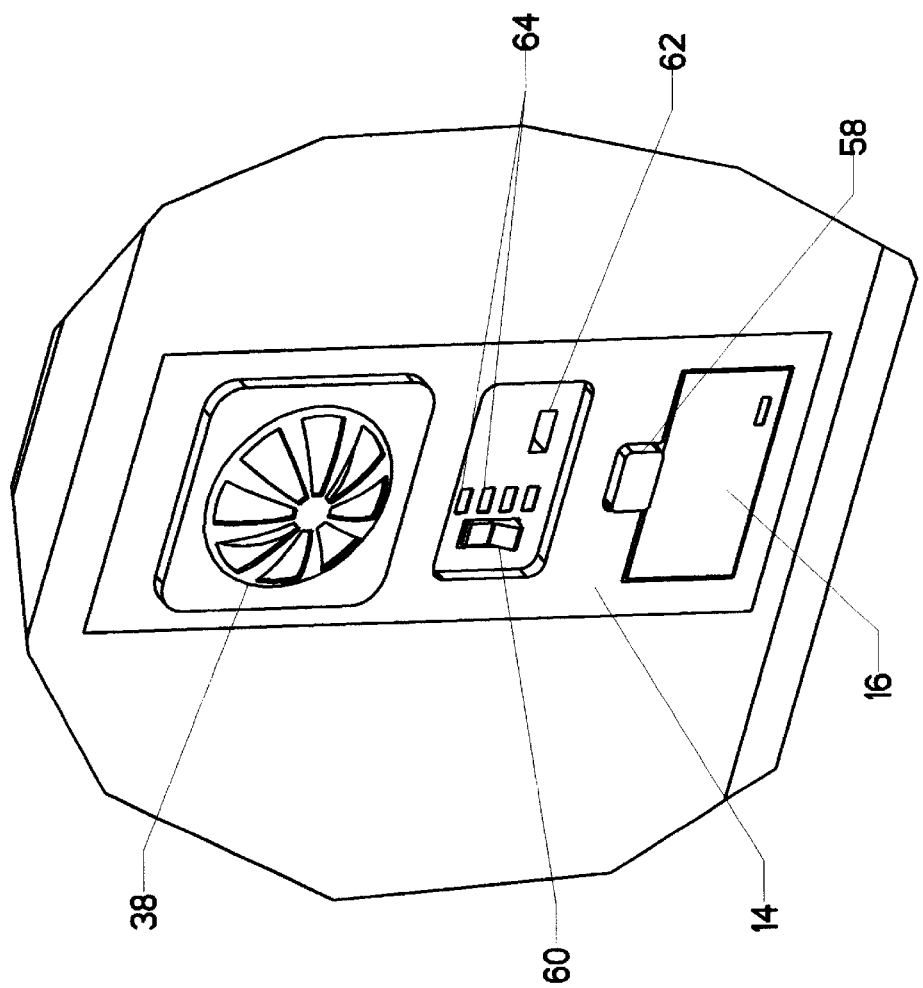
FIG. 5 is an isometric view, showing details of the control panel.

FIG. 5 shows a detailed view of the front of cooling module 14. Battery 16 is shown in its bay within cooling module 14. Once the user slides battery 16 into its bay, it is retained by a conventional catch mechanism. If the user wishes to remove battery 16, he or she presses battery release 58, which ejects battery 16 outward a short distance. The user then grasps battery 16 and manually removes it.

The front face of cooling module 14 is provided with power switch 60. In the embodiment shown, once power switch 60 is pressed to the "on" position, thermostatic control means are engaged to maintain the interior of chassis 12 at a fixed temperature—such as 40 degrees F. Additional user inputs may be provided to allow the user to adjust the maintained temperature. However, as the invention is intended to be used primarily with blood and urine samples, it is advantageous to have a non-adjustable temperature (thereby eliminating a possibility of human error).

Indicator lights 64 are provided to inform the user whether the device is on or off, to provide battery charge status, etc. Power input 62 is a female receptacle intended to receive external DC electrical power. Different adapters are provided so that the transporter can be plugged into an automobile cigarette lighter or a 110 VAC wall outlet (through the use of an external AC to DC transformer/rectifier). As these adapters are well known in the prior art, they have not been illustrated.

However, it is important to appreciate the utility provided by the combination of battery 16 and power input 62. The user typically takes transporter 10 to several sites for collection of specimens. He or she would routinely leave transporter 10 plugged into a wall outlet in the office in order to cool the interior to the desired temperature prior to departing for the first collection. When the user unplugs transporter 10, control means automatically switch it to internal battery power. Once in a vehicle, the user plugs transporter 10 into the cigarette lighter, whereupon control means automatically switch it back to external power. One at the collecting site, the user may elect—if the collections are likely to be over an extended period—to again plug transporter 10 into a wall outlet. In this manner, the reduced temperature inside transporter 10 can be maintained indefinitely.

Figure 6:
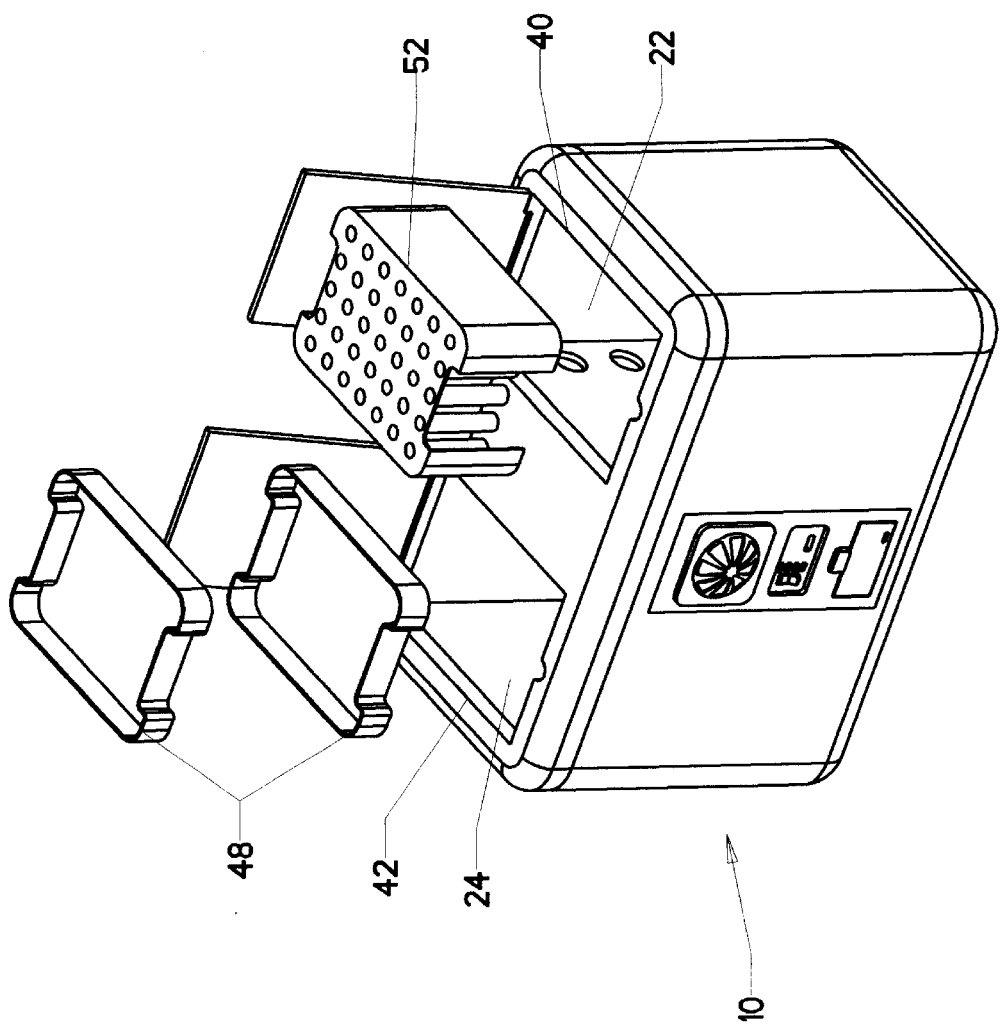
FIG. 6 is an isometric view, showing specimen trays being placed in the transporter.

FIG. 6 shows transporter 10 with both hatch covers open. Urine sample trays 48 are carefully sized to fit through left hatch 42 and stack within urine sample well 24 (specimen cups and bags are placed within each urine sample tray 48 before it is stacked in urine sample well 24). Likewise, blood sample tray 52 is carefully sized to fit through right hatch 40 and stack within blood sample well 22 (blood vials are placed within blood sample tray 52 before it is stacked in blood sample well 22). The reader should note that although only one blood sample tray 52 is shown, two or more can be stacked within blood sample well 22. The reader will observe that the rectangular perimeter of both types of sample trays will be held firmly by the rectangular walls of the well in which it is placed. The reader will also observe that both types of sample trays are designed to stack. The use of the trays allows the user to secure many small sample containers within the relatively spacious interior of transporter 10.

Urine sample trays 48 are in fact an optional feature of the invention. Depending on the type of collection bags employed, the user may find it more convenient to simply place the urine sample bags directly into urine sample well 24.

Figure 7:
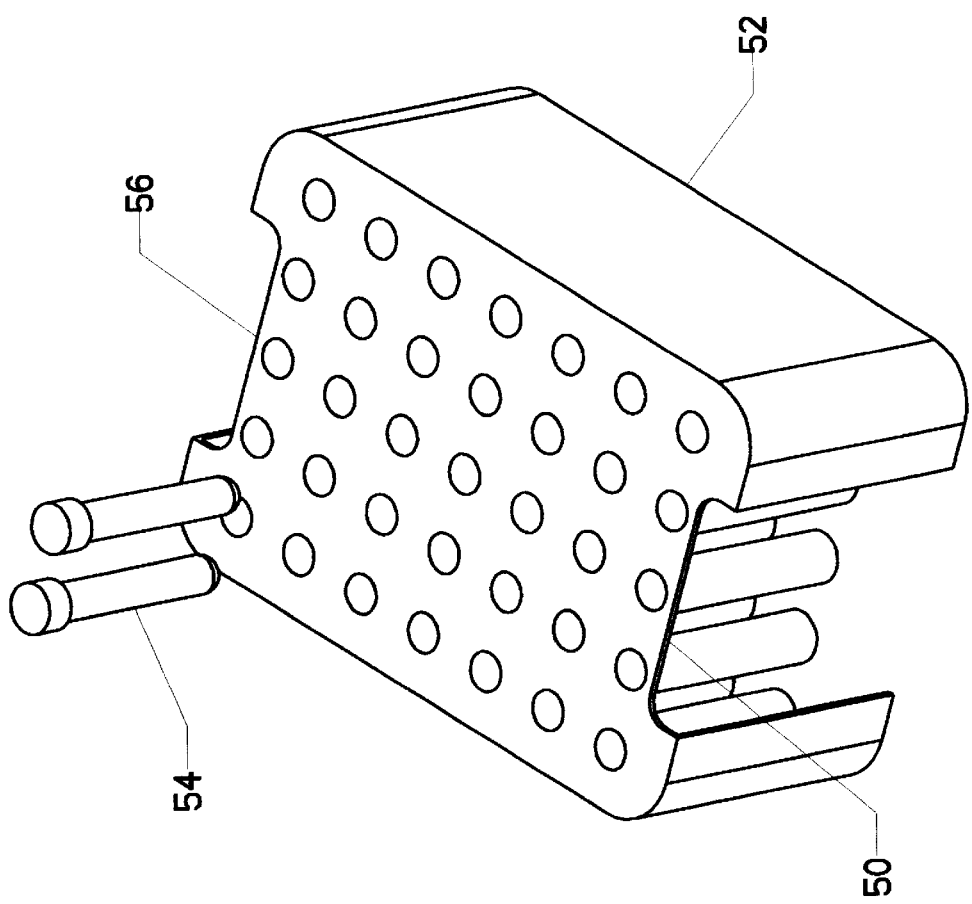
FIG. 7 is an isometric view, showing details of the blood specimen tray.

FIG. 7 is a detailed view of blood sample tray 52. Its upper surface opens into a grid of via cavities 56. Each via cavity 56 is shaped to receive and securely hold a blood via 54. Thus, once a blood sample has been collected in blood via 54, the user deposits it in a via cavity 56. The configuration of blood sample tray 52—being a thin walled structure—is such that it can easily be made of injection-molded plastic.

Finger notches 50 are provided on either side of blood sample tray 52. These are provided so that the user can grasp and remove blood sample tray 52 from blood sample well 22. Because of the fact that blood sample tray 52 fits snugly within blood sample well 22, it would be difficult to remove the tray without finger notches 50.

Figure 8:
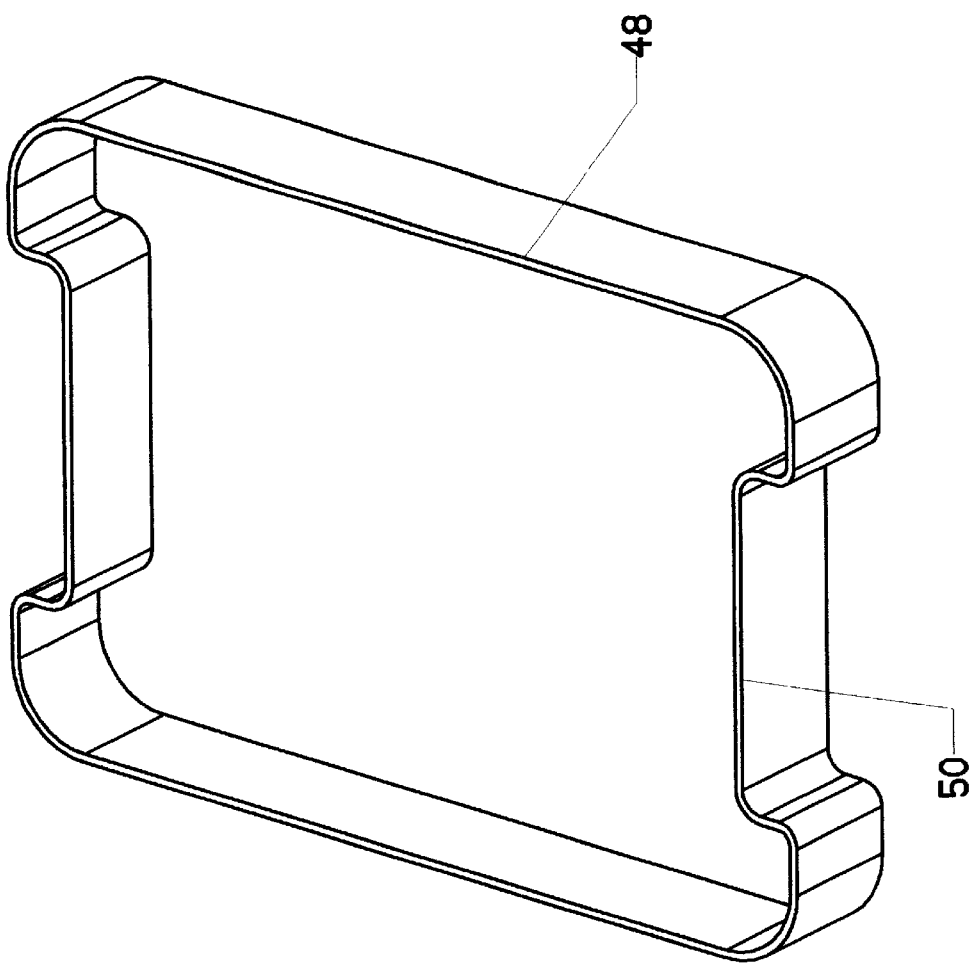
FIG. 8 is an isometric view, showing details of the urine specimen tray.

FIG. 8 is a detailed view of urine sample tray 48. Urine samples are typically collected in small cups, after which they are placed in a sealed plastic bag. Urine sample tray 48 is designed to receive one or more such bags. Once the bag or bags have been placed within urine sample tray 48, urine sample tray 48 is placed within urine sample well 24. Finger notches are also provided to ease the removal of urine sample tray 48 from transporter 10. It also has a thin-walled structure to facilitate its manufacture as an injection molded part.

The previous portions of the description have explained how the invention stores and transports biological specimens at a reduced temperature. However, those skilled in the art will realize that security is a significant concern with the transportation of such samples. Biological samples are often used in courts of law. In order to be introduced as evidence, a clear chain of custody must be maintained. This means that the individual collecting the specimens must be able to ensure that no unauthorized access to the specimens is allowed.

Since a collection transporter must be portable, it is impractical to have a truly secure structure. One cannot carry a steel safe. However, it is sufficient to provide a securing means which will clearly indicate if the transporter has been opened in the user's absence. The user would then know that the samples contained within the transporter can no longer be considered valid.

Figure 9:
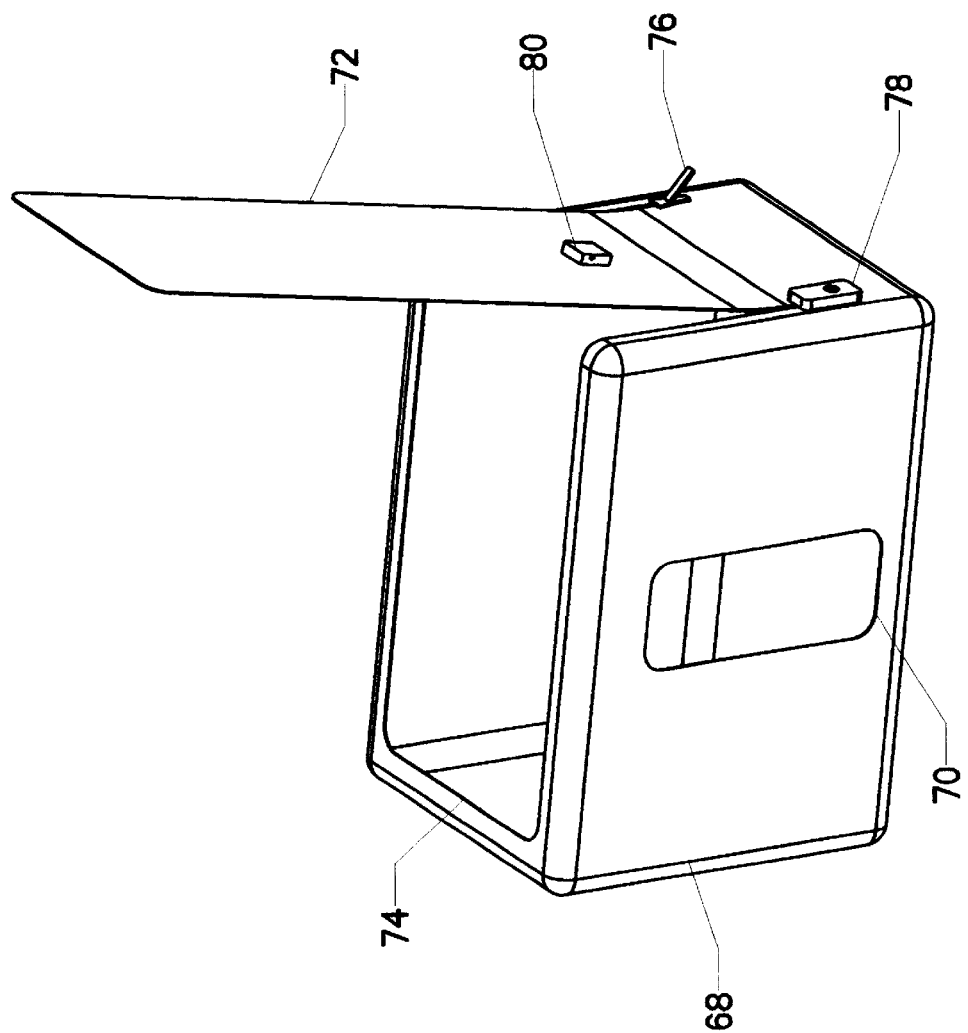
FIG. 9 is an isometric view, showing a fabric cover.
Figure 10:
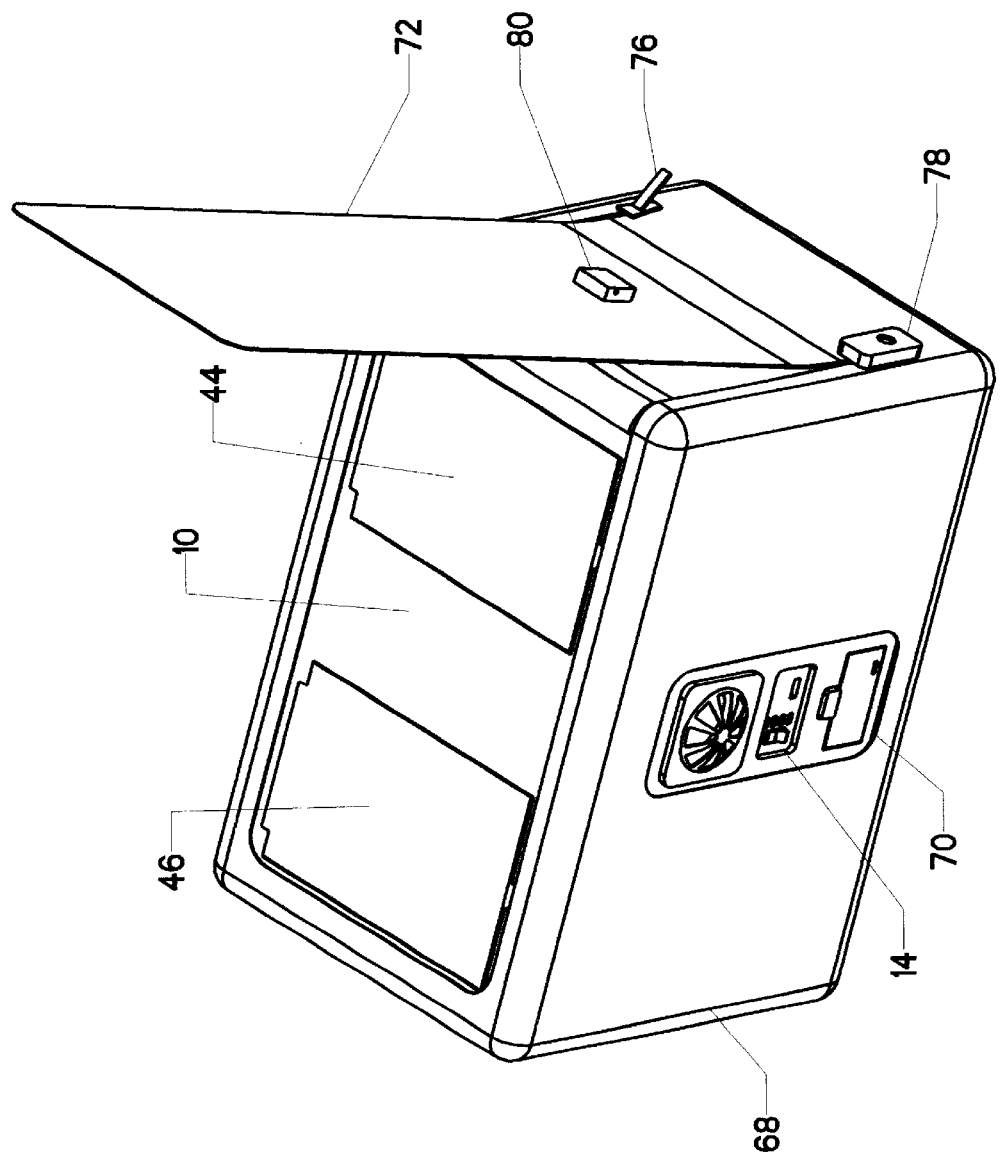
FIG. 10 is an isometric view, showing the fabric cover of FIG. 9 placed on the transporter.

FIG. 9 shows one such securing device. Fabric cover 68 is designed to slip over transporter 10. It is typically made of a durable fabric, such as KEVLAR or BALLISTIC NYLON. FIG. 10 shows fabric cover 68 in place on transporter 10. Returning now to FIG. 9, the features of fabric cover 68 will be explained in detail. Fabric cover 68 is made in a hollow rectangular shape, with an opening large enough to admit transporter 10. The opening is closed via securing flap 72. The reader will observe that zipper track 74 runs completely around the perimeter of the opening. The user pulls zipper handle 76 to close securing flap 72. When the zipper has traveled completely around zipper track 74, it comes to rest within zipper lock 78. Zipper lock 78 is a conventional prior art device—as found on bank cash bags and the like. It has a key lock (some have combinations and push buttons) which locks the zipper in place. The zipper can then only be opened by someone having the key.

Turning back to FIG. 10, the operation of fabric cover 68 will be explained. With securing flap 72 in the open position—as shown—the user has access to open the hatch covers and add or remove samples within transporter 10. If however, the user must leave transporter 10 unattended for a few moments, he or she may secure it by zipping securing flap 72 in place and locking zipper lock 78. It is then very difficult to gain entrance to transporter 10 without visibly damaging fabric cover 68.

Figure 11:
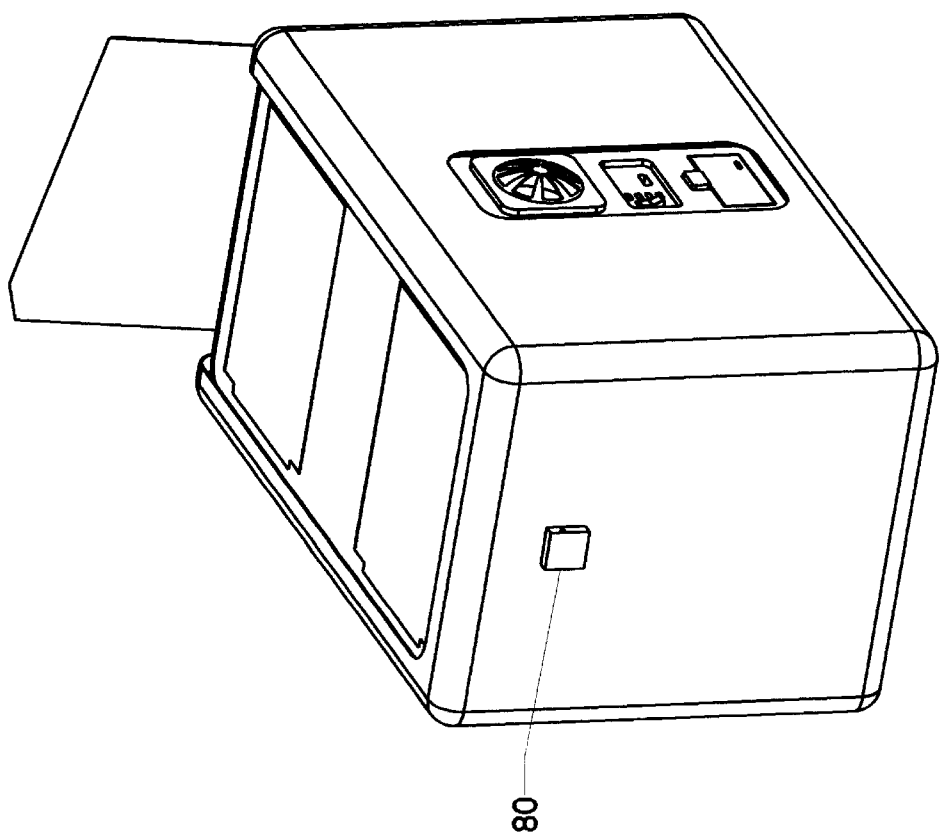
FIG. 11 is an isometric view, showing the configuration of FIG. 10 from another perspective.

The reader will observe that access hole 70 is provided in fabric cover 68 to allow access to the front of cooling module 14. The reader will also observe the presence of strap attachment 80. This feature is provided to allow the attachment of a shoulder strap (not shown). FIG. 11 illustrates that the opposite end of fabric cover 68 is equipped with a second strap attachment 80. The user may therefore attach a shoulder strap to both ends of fabric cover 68 and use it to conveniently carry transporter 10. As such straps are well known in the prior art, a particular strap has not been illustrated.

SUMMARY, RAMIFICATIONS, AND SCOPE

Accordingly, the reader will appreciate that the proposed invention can securably store and transport biological samples. The invention has further advantages in that it:

1. Can maintain reduced storage temperatures indefinitely;
2. Provides effective anti-tamper means;
3. Can be opened regularly to admit new specimens;
4. Provides separate storage areas for different types of specimens; and
5. Can be powered by a variety of power sources.

Although the preceding description contains significant detail, it should not be construed as limiting the scope of the invention but rather as providing illustrations of the preferred embodiment of the invention. Thus, the scope of the invention should be fixed by the following claims, rather than by the examples given.

Having described my invention, I claim:

1. A securable device for transporting biological specimens while maintaining said specimens at a reduced temperature, comprising:
   a. an essentially rectangular chassis having an insulated bottom wall and insulated side walls extending upward therefrom to form a hollow interior having an upward-facing opening, wherein said hollow interior is capable of receiving said biological specimens;
   b. at least one bulkhead dividing said hollow interior into at least two wells;
   c. a top, covering said upward-facing opening, and containing at least two hatches providing access to said at least two wells;
   d. at least two hatch covers covering said at least two hatches;
   e. cooling means for cooling said hollow interior; and
   f. securing means for prohibiting unauthorized opening of said at least two hatch covers, thereby prohibiting unauthorized access to said biological specimens within said hollow interior.

2. The device as recited in claim 1, having at least one removable sample tray configured to fit securely within one of said at least two wells.

3. The device as recited in claim 2, further comprising at least one more removable sample tray, wherein said at least two sample trays are configured to stack one upon the other within one of said at least two wells.

4. The device as recited in claim 1, wherein said securing means comprises a fabric cover fitting over said rectangular chassis and having a securing flap lockably securable over said at least two hatch covers.

5. The device as recited in claim 1, further comprising a document slot having access through said top.

* * * * *